(12) United States Patent
Slaugh et al.

(10) Patent No.: US 6,180,838 B1
(45) Date of Patent: Jan. 30, 2001

(54) PROCESS FOR PREPARING ALKANEDIOLS

(75) Inventors: Lynn Henry Slaugh; Paul Richard Weider; Joseph Broun Powell, all of Houston, TX (US)

(73) Assignee: Shell Oil Company, Houston, TX (US)

( * ) Notice: Under 35 U.S.C. 154(b), the term of this patent shall be extended for 0 days.

(21) Appl. No.: 08/618,734

(22) Filed: Mar. 20, 1996

Related U.S. Application Data

(63) Continuation-in-part of application No. 08/316,676, filed on Sep. 30, 1994.

(51) Int. Cl.$^7$ .................................................. C07C 27/04
(52) U.S. Cl. ........................................... 568/862; 568/483
(58) Field of Search .................................... 568/852, 862, 568/483

(56) References Cited

U.S. PATENT DOCUMENTS

| | | | |
|---|---|---|---|
| 3,687,981 | 8/1972 | Lawrence | 260/340.7 |
| 4,873,379 | 10/1989 | Murphy | 568/867 |
| 4,935,554 | 6/1990 | Murphy et al. | 568/867 |
| 4,973,741 | 11/1990 | Beavers | 560/179 |
| 5,030,766 | 7/1991 | Briggs | 568/496 |
| 5,043,480 | 8/1991 | Beavers | 568/496 |
| 5,053,562 | 10/1991 | Tau | 568/867 |
| 5,135,901 | 8/1992 | Beavers | 502/161 |
| 5,210,318 | 5/1993 | Briggs | 568/496 |
| 5,225,387 | 7/1993 | Briggs | 502/167 |
| 5,256,827 | 10/1993 | Slaugh | 568/454 |
| 5,426,249 | 6/1995 | Haas et al. | 568/862 |
| 5,463,146 | 10/1995 | Slaugh et al. | 568/862 |

*Primary Examiner*—Rebecca Cook

(57) ABSTRACT

An alkanediol such as 1,3-propanediol is prepared in a process which involves reacting an alkylene oxide with carbon monoxide and hydrogen in an essentially non-water-miscible solvent in the presence of a non-phosphine-ligated rhodium catalyst and a catalyst promoter to produce an intermediate product mixture containing a hydroxyalkanal in an amount less than 15 wt %; extracting the hydroxyalkanal from the intermediate product mixture into an aqueous liquid at a temperature less than about 100° C. and separating the aqueous phase containing hydroxyalkanal from the organic phase containing rhodium catalyst; hydrogenating the hydroxyalkanal in the aqueous phase to an alkanediol; and recovering the alkanediol.

The process enables the production of an alkanediol such as 1,3-propanediol in high yields and selectivity without the use of a phosphine ligand-modified rhodium catalyst.

18 Claims, 1 Drawing Sheet

PROCESS FOR PREPARING ALKANEDIOLS

CROSS-REFERENCE TO RELATED APPLICATION

This application is a continuation-in-part of Ser. No. 316,676, filed Sep. 30, 1994 abandoned.

BACKGROUND OF THE INVENTION

This invention relates to the preparation of alkanediols including 1,3-propanediol. In a specific aspect, the invention relates to a rhodium-catalyzed process for manufacturing 1,3-propanediol in high yields without the use of a phosphine ligand for the rhodium catalyst.

1,3-propanediol (PDO) is an intermediate in the production of polyesters for fibers and films. It is known to prepare PDO in a two-step process involving (1) the rhodium-catalyzed hydroformylation (reaction with synthesis gas, $H_2/CO$) of ethylene oxide to intermediate 3-hydroxypropanal (HPA) and (2) hydrogenation of the HPA to PDO. The initial hydroformylation step can be carried out at temperatures greater than 100° C. and at high syngas pressures to achieve practical reaction rates. The resulting product mixture is, however, rather unselective for HPA.

In an alternate hydroformylation method, the rhodium catalyst is used in combination with a phosphine ligand to prepare HPA with greater selectivity and at lower temperature and pressure. However, the use of a phosphine ligand adds to the cost of the catalyst and increases the complexity of catalyst recycle.

It would be desirable to prepare PDO and other alkanediols in a low temperature, selective process which permitted efficient recycle of the rhodium catalyst.

It is therefore an object of the invention to provide a process for the preparation of alkanediols. In a specific embodiment, it is an object of the invention to provide an economical process for the preparation of 1,3-propanediol which does not require the use of a phosphine-ligated rhodium catalyst for preparation of the HPA intermediate.

SUMMARY OF THE INVENTION

According to the invention, an alkanediol is prepared in a process comprising the steps of:

(a) contacting an alkylene oxide with carbon monoxide and hydrogen in an essentially non-water-miscible solvent in the presence of an effective amount of a non-phosphine-ligated rhodium catalyst and an effective amount of a catalyst promoter at a temperature within the range of about 90 to about 125° C. and a pressure within the range of about 15 to about 5000 psig, under reaction conditions effective to produce an intermediate product mixture comprising less than 15 wt % hydroxyaldehyde;

(b) adding an aqueous liquid to said intermediate product mixture and extracting into said aqueous liquid at a temperature less than about 125° C. a major portion of the hydroxyaldehyde to provide an aqueous phase comprising hydroxyaldehyde in greater concentration than the concentration of hydroxyaldehyde in said intermediate product mixture, and an organic phase comprising at least a portion of the rhodium catalyst or a rhodium-containing derivative thereof;

(c) separating the aqueous phase from the organic phase;

(d) contacting the aqueous phase comprising hydroxyaldehyde with hydrogen in the presence of a hydrogenation catalyst at a pressure of at least about 100 psig and a temperature during at least a portion of the hydrogenation step of at least 40° C. to provide a hydrogenation product mixture comprising an alkanediol; and (e) recovering the alkanediol from said hydrogenation product mixture.

The process enables the production of alkanediols such as 1,3-propanediol in high yields and selectivity without the use of a phosphine-ligated rhodium catalyst in the hydroformylation step.

DETAILED DESCRIPTION OF THE INVENTION

Figure 1:
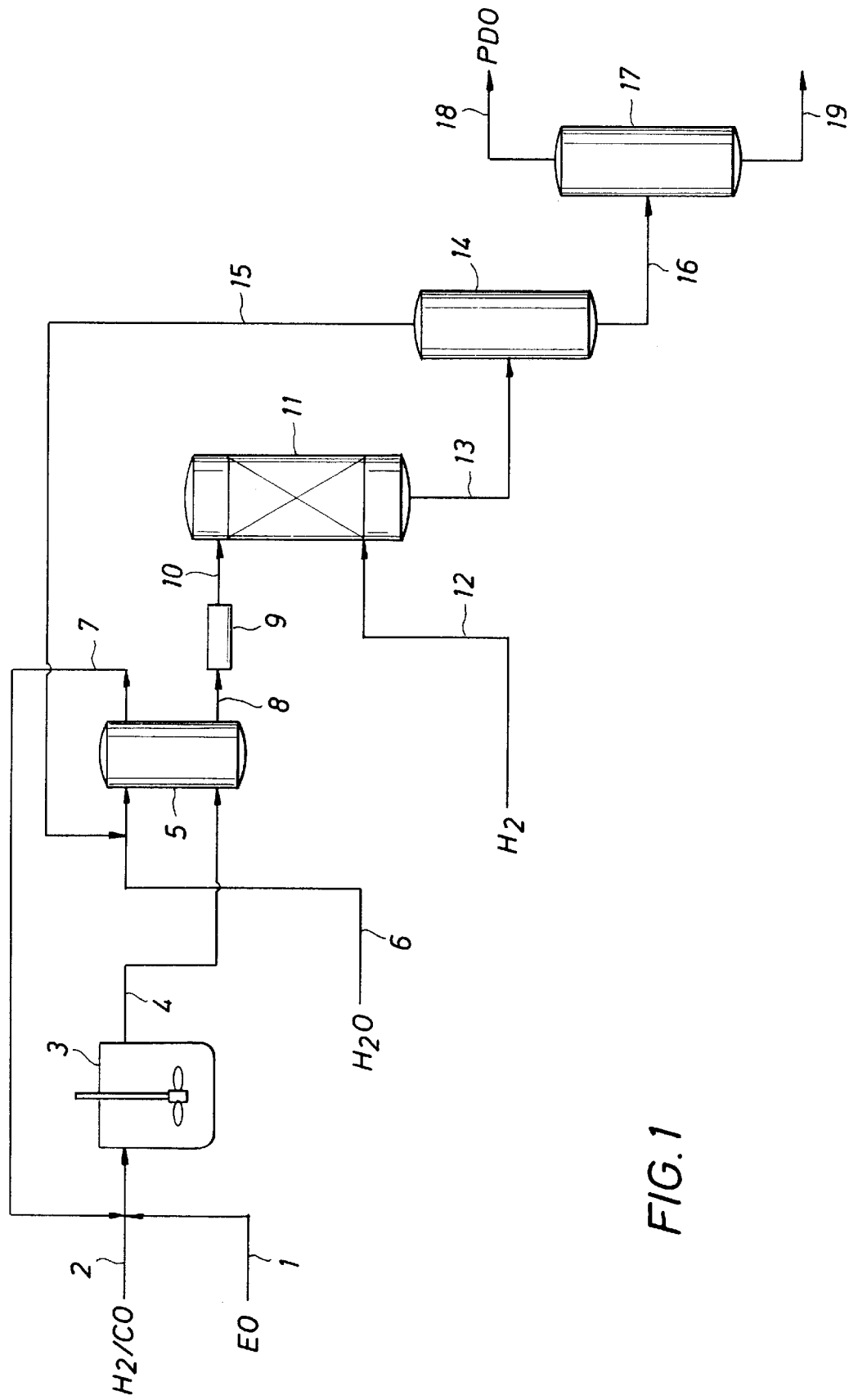
FIG. 1 is a schematic flow diagram of one embodiment of the invention alkanediol preparation process.

In the invention process, an alkylene oxide is reacted with carbon monoxide and hydrogen to produce an intermediate hydroxyaldehyde, which is then hydrogenated to the desired alkanediol. Suitable alkylene oxide starting materials can be described by the formula $RCHOCH_2$, in which R is hydrogen (ethylene oxide) or $C_{1-3}$ alkyl (propylene oxide, butylene oxide, pentylene oxide). The intermediate hydroxyaldehyde can be represented by the formula

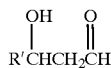

in which R' is hydrogen or $C_{1-3}$ alkyl including, for example, hydroxyaldehydes such as 3-hydroxypropanal, 3-hydroxybutanal, 3-hydroxypentanal, and 3-hydroxyhexanal.

Correspondingly, the alkanediol can be represented by the formula

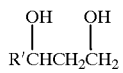

where R' is as described above. Such alkanediols include 1,3-propanediol, 1,3-butanediol, 1,3-pentanediol and 1,3-hexanediol. For simplicity, the process will be described, by reference to FIG. 1, in terms of starting with ethylene oxide to produce 1,3-propanediol.

In FIG. 1, separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a non-phosphine-ligated rhodium catalyst, i.e., a rhodium carbonyl composition which has not been prereacted with a phosphine ligand. The hydrogen and carbon monoxide will generally be introduced into the reaction vessel in a molar ratio within the range of about 1:2 to about 8:1, preferably about 1.5:1 to about 5:1.

The reaction is carried out under conditions effective to produce a hydroformylation reaction product mixture containing a major portion of 3-hydroxypropanal (HPA) and diol and a minor portion of acetaldehyde, while maintaining the level of 3-hydroxypropanal in the reaction mixture at less than 15 wt %, preferably within the range of about 5 to about 10 wt %. (To provide for solvents having different densities, the desired concentration of HPA in the reaction mixture can be expressed in molarity, i.e., less than 1.5M, preferably within the range of about 0.5 to about 1M.) Generally, the hydroformylation reaction is carried out at elevated temperature less than 125° C., preferably about 100 to about 115° C., and at a pressure within the range of about 15 to about 5000 psig, preferably (for process economics) about 15 to about 1000 psig. The concentration of 3-hydroxypropanal in the intermediate product mixture can be controlled by regulation of process conditions such as ethylene oxide concentration, catalyst concentration, reaction temperature and residence time. In the practice of the invention method, it is possible to achieve product (HPA plus PDO) yields (based on ethylene oxide conversion) of greater than 70%, with formation of greater than 7 wt % product, at rates greater than 15 h$^{-1}$. (Catalytic rates are referred to herein in terms of "turnover frequency" or "TOF" and are expressed in units of moles per mole of rhodium per hour, or h$^{-1}$.)

The hydroformylation reaction is carried out in a liquid solvent inert to the reactants. By "inert" is meant that the solvent is not consumed during the course of the reaction. In general, ideal solvents for the phosphine ligand-free process will solubilize carbon monoxide, will be essentially non-water-miscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt %, so as to form a separate hydrocarbon-rich phase upon water extraction of HPA from the hydroformylation reaction mixture. Preferably this solubility is less than about 10%, most preferably less than about 5 wt %. The solubilization of carbon monoxide in the selected solvent will generally be greater than 0.15 v/v (1 atm, 25° C.), preferably greater than 0.25 v/v, as expressed in terms of Ostwald coefficients.

The preferred class of solvents are alcohols and ethers which can be described according to the formula $$R_2\text{—}O\text{—}R_1 \qquad (1)$$

in which $R_1$ is hydrogen or $C_{1\text{-}20}$ linear, branched, cyclic or aromatic hydrocarbyl or mono- or polyalkylene oxide and $R_2$ is $C_{1\text{-}20}$ linear, branched, cyclic or aromatic hydrocarbyl, alkoxy or mono- or polyalkylene oxide. The most preferred hydroformylation solvents can be described by the formula (2)

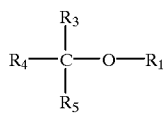

in which $R_1$ is hydrogen or $C_{1\text{-}8}$ hydrocarbyl and $R_3$, $R_4$ and $R_5$ are independently selected from $C_{1\text{-}8}$ hydrocarbyl, alkoxy and alkylene oxide. Such ethers include, for example, methyl-t-butyl ether, ethyl-t-butyl ether, diethyl ether, phenylisobutyl ether, ethoxyethyl ether, diphenyl ether and diisopropyl ether. Blends of solvents such as tetrahydrofuran/toluene, tetrahydrofuran/ heptane and t-butylalcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated rhodium carbonyl compound. Although phosphine-ligated catalysts are active for hydroformylation reactions, the invention process is designed to achieve good yield and selectivity without the additional expense of the ligand. The rhodium catalyst can be supplied to the hydroformylation reactor in essentially any form including metal, supported metal, hydroxide, chloride, oxide, carbonate, sulfate, acetylacetonate, salt of a carboxylic acid, or as an aqueous rhodium salt solution, for example. It may be supplied directly as a rhodium carbonyl such as tetrarhodium dodecacarbonyl or dicarbonylacetylacetonato rhodium. If not supplied in the latter form, operating conditions can be adjusted such that rhodium carbonyls are formed in situ via reaction with $H_2$ and CO, as described in Wender and Pino, "Organic Synthesis via Metal Carbonyls," Vol. 1, pp. 1–273, Interscience Publishers (1968). For more rapid reaction, temperatures of about 120 to 200° C. should be employed, at CO pressures of at least 500 psig. Addition of high surface area activated carbons or zeolites, especially those containing or supporting platinum or palladium metal, can accelerate rhodium carbonyl formation from noncarbonyl precursors. The resulting catalyst is maintained under a stabilizing atmosphere of carbon monoxide, which also provides protection against exposure to oxygen. The most economical and preferred catalyst activation and reactivation (of recycled catalyst) method involves preforming the rhodium salt (or derivative) under $H_2$/CO in the presence of the catalyst promoter employed for hydroformylation. The conversion of $Rh^{2+}$ to the desired rhodium carbonyl can be carried out from rhodium chloride at a temperature within the range of about 50 to about 80° C., and a syn gas pressure within the range of about 500 to about 3500 psig for a time preferably less than about 3 hours. The preforming step can be carried out in a pressurized preforming reactor or in situ in the hydroformylation reactor.

The amount of rhodium present in the reaction mixture will vary depending upon the other reaction conditions, but will generally fall within the range of about 0.01 to about 1 wt %, preferably about 0.05 to about 0.3 wt %, based on the weight of the reaction mixture.

The hydroformylation reaction mixture will preferably include a catalyst promoter to accelerate the reaction rate. Suitable promoters include sources of monovalent metal cations of weak bases such as alkali metal salts of carboxylic acids. Also suitable are lipophilic promoters such as lipophilic phosphonium salts, which accelerate the rate of hydroformylation without imparting hydrophilicity (water solubility) to the active catalyst. As used herein, "lipophilic" means that the promoter tends to remain in the organic phase after extraction of HPA and diol with water. The promoter will generally be present in an amount within the range of about 0.01 to about 2.0 moles per mole of rhodium. Suitable metal salts include sodium, lithium, potassium and cesium acetates, propionates and octoates. The currently preferred metal salt, because of its availability and demonstrated promotion of ethylene oxide hydroformylation, is lithium iodide. The currently preferred lipophilic promoter is tetrabutylphosphonium acetate.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired rhodium carbonyl catalyst species. Acceptable water levels will depend upon the solvent used, with more polar solvents generally being more tolerant of higher water concentrations. For example, optimum water levels for hydroformylation in methyl-t-butylether solvent are believed to be within the range of about 1 to about 2.5 wt %.

Following the hydroformylation reaction, hydroformylation reaction product mixture 4 containing 3-hydroxypropanal, the reaction solvent, 1,3-propanediol, the rhodium catalyst and a minor amount of reaction by-products, is cooled and passed to extraction vessel 5, wherein an aqueous liquid, generally water and optional miscibilizing solvent, are added via 6 for extraction and concentration of the HPA for the subsequent hydrogenation step. Liquid extraction can be effected by any suitable means, such as mixer-settlers, packed or trayed extraction columns, or rotating disk contactors. Extraction can, if desired, be carried out in multiple stages. The water-containing hydroformylation reaction product mixture can optionally be passed to a settling tank (not shown) for resolution of the mixture into aqueous and organic phases. The amount of water added to the hydroformylation reaction product mixture will generally be such as to provide a water:mixture ratio within the range of about 1:1 to about 1:20, preferably about 1:5 to about 1:15. The addition of water at this stage of the reaction may have the additional advantage of suppressing formation of undesirable heavy ends. Extraction with a relatively small amount of water provides an aqueous phase which is greater than 20 wt % HPA, preferably greater than 25 wt % HPA, permitting economical hydrogenation of the HPA to PDO and recovery of PDO product. The water extraction is preferably carried out at a temperature within the range of about 25 to about 125° C., with higher temperatures avoided to minimize condensation products (heavy ends) and catalyst loss. In order to maximize catalyst recovery, it is optional but preferred to perform the water extraction under 50 to 200 psig carbon monoxide at 25 to 55° C. Additional water extraction(s) may be desirable, particularly for higher molecular weight hydroxyaldehydes, to remove essentially all of the intermediate from the solvent phase.

The organic phase containing the reaction solvent and the major portion of the rhodium catalyst can be recycled from the extraction vessel to the hydroformylation reaction via 7. Aqueous extract 8 is optionally passed through one or more acid ion exchange resin beds 9 (or other suitable absorption material) for removal of any rhodium catalyst present, and the demetallized aqueous product mixture 10 is passed to hydrogenation vessel 11 and reacted with hydrogen 12 in the presence of a hydrogenation catalyst to produce a hydrogenation product mixture 13 containing 1,3-propanediol. The hydrogenation step may also revert some heavy ends to PDO. The solvent and extractant water 15 can be recovered by distillation in column 14 and recycled to the water extraction process via a further distillation (not shown) for separation and purge of light ends. PDO-containing product stream 16 can be passed to distillation column 17 for recovery of PDO 18 from heavy ends 19.

Hydrogenation of the HPA to PDO can be carried out in aqueous solution at an elevated temperature during at least a portion of the hydrogenation step of about 40° C., generally within the range of about 50 to about 175° C., under a hydrogen pressure of at least about 100 psig, generally within the range of about 200 to about 2000 psig. The reaction is carried out in the presence of a hydrogenation catalyst such as any of those based upon Group VIII metals, including nickel, cobalt, ruthenium, platinum and palladium, as well as copper, zinc and chromium and mixtures and alloys thereof. Nickel catalysts, including bulk or supported, and fixed-bed and slurry forms, provide acceptable activities and selectivities at moderate cost.

Commercial operation will require efficient rhodium catalyst recovery with essentially complete recycle of rhodium to the hydroformylation reaction. The preferred catalyst recovery process involves two steps, beginning with the above-described water extraction of HPA from the hydroformylation product mixture. A major portion of the rhodium catalyst will remain in the organic phase, with the remaining rhodium catalyst passing into the water phase. The organic phase can be recycled to the hydroformylation reactor, with optional purge of heavy ends. Optionally, further demetallizing of the water layer can be effected by any suitable method, such as complete or partial oxidation of rhodium followed by precipitation and filtration, distillation, deposition on a solid support, or extraction using a suitable extractant, preferably prior to final removal by ion exchange (9).

The invention process permits the selective and economic synthesis of PDO at moderate temperatures and pressures without the use of a phosphine ligand for the hydroformylation catalyst. The process involves preparation of a reaction product mixture dilute in intermediate HPA, then concentration of this HPA by water extraction followed by hydrogenation of the aqueous HPA to PDO.

EXAMPLE 1

This example illustrates the rhodium-catalyzed hydroformylation of propylene oxide in accordance with the invention process.

A 100-ml Parr autoclave was charged with 85 mg (0.33 mmole) of dicarbonylacetylacetonato rhodium (I), 106 mg (0.28 mmole) of tetrabutylphosphonium acetate monoacetic acid and 34 ml of water-saturated (about 2 wt %), nitrogen-purged methyl-t-butylether. The contents of the autoclave were stirred under an inert atmosphere at 110° C. for one hour under 1300 psig $H_2/CO$ (2:1). The reactor was cooled to 50° C. and vented to ambient pressure. 1.98 g propylene oxide (34 mmole) were injected into the reactor. The reaction solution was stirred and heated at 110° C. and 1500 psig $H_2/CO$ (2:1) for 5 hours and then cooled to 5° C. The gases were slowly vented to ambient pressure, and 25 ml of nitrogen-purged, deionized water were injected into the reactor. After stirring for 5 minutes and allowing phase separation, the water phase was removed from the reactor and was analyzed by gas chromatography. Results are shown in Table 1.

1.98 g fresh propylene oxide (34 mmole) was injected into the reactor and the reaction solution was heated with stirring for 5 hours at 110° C. and 1500 psig $H_2/CO$ (2:1). The reaction was cooled, vented and extracted with deionized water under an inert atmosphere as described above. The phases were analyzed for product content by gas chromatography, and each phase was also analyzed for rhodium. Results are shown in Table 1 (runs designated "R").

were charged to the reaction vessel at 110° C. and the pressure was further increased to 1500 psig $H_2/CO$ (2:1). Stirring was continued for 5 hours at 110° C. and 1500 psig. The reaction was cooled to 5° C. Gases were slowly vented to ambient pressure, and 15 ml of nitrogen-purged, deionized water were charged to the reactor. After stirring for 5 minutes, the reactor was moved to a nitrogen box for phase separation by separatory funnel. The phases were analyzed by gas chromatography. Results are shown in Table 2.

To examine recycle of the organic phase, the methyl-t-butyl ether phase was reloaded into the autoclave and stirred at 110° C. and 800 psig $H_2/CO$ (2:1) for 30 minutes. 1.5 g (34 mmole) of ethylene oxide were charged to the autoclave with stirring at 110° C., and the pressure was further increased to 1500 psig. The reaction solution was stirred at 110° C. under 1500 psig $H_2/CO$ (2:1) for 5 hours, then cooled to 5° C., vented, extracted with deionized water and phase separated under an inert atmosphere. The two phases were analyzed for rhodium content and, by gas chromatography, for product content. Results are shown in Table 2 (runs designated "R").

TABLE 1

Hydroformylation of Propylene Oxide (PO)

| Catalyst[e] (mmoles) | Promoter (mmoles) | PO Conv. (%) | Selectivity, (mole %)[a] | | | | | | % of Catalyst Remaining in MTBE[d] After RXN |
|---|---|---|---|---|---|---|---|---|---|
| | | | DMK | 3-HBA | 1,3-BDO | 2-Me3-HPA | Dimers | Others | |
| Rh(CO)$_2$AcAc[b] 0.33 | Bu$_4$POAc[c] 0.28 | 22 | 19.8 | 4.9 | 60.8 | 3.3 | 6.6 | 4.6 | |
| Rh(CO)$_2$AcAc[b] R 0.33 | Bu$_4$POAc[c] 0.28 | 51 | 6.9 | 40.2 | 51.9 | — | 1.0 | | 99.4 |
| Rh(CO)$_2$AcAc[b] 0.33 | None | 4 | 1.5 | 98.5 | — | — | — | | |
| Rh(CO)$_2$AcAc[b] R 0.33 | " | 4 | — | 89.5 | — | — | — | 10.5 | 96.7 |

[a]DMK is dimethylketone (acetone); 3-HBA is 3-hydroxybutyraldehyde; 1,3-BDO is 1,3-butanediol; 2-Me-3-HPA is 2-methyl-3-hydroxypropionaldehyde.
[b]Rh(CO)$_2$AcAc is dicarbonylacetylacetonato rhodium (I).
[c]Bu$_4$POAc is tetra-n-butylphosphonium acetate monoacetic acid.
[d]MTBE = methyl-t-butyl ether solvent.
[e]R in this column designates experiments using recycled rhodium catalyst present in the phase-separated methyl-t-butyl ether recovered from the experiment immediately above in the table.

EXAMPLE 2:

This example illustrates rhodium-catalyzed hydroformylation of ethylene oxide according to the invention process.

To the reactor system of Example 1 were charged 85 mg (0.33 mmole) of dicarbonylacetylacetonato rhodium (I), 34 ml of water-saturated, nitrogen-purged methyl-t-butyl ether and the indicated amount of promoter (in addition to water). The reaction mixture was stirred at 110° C. under 800 psig $H_2/CO$ (2:1) for 1 hour. 1.5 g (34 mmole) of ethylene oxide

TABLE 2

Hydroformylation of Ethylene Oxide (EO)

| Catalyst[e] (mmoles) | Promoter (mmoles) | EO Conv. (%) | Selectivity, (mole %) | | | | | % of Catalyst Remaining in MTBE[d] After RXN |
|---|---|---|---|---|---|---|---|---|
| | | | AA[b] | 3-HPA[b] | 1,3-PDO[b] | Unknown | Oligomers | |
| Rh(CO)$_2$AcAc[a] 0.33 | None | 4 | 17.6 | — | — | 49.7 | 32.7 | |
| Rh(CO)$_2$AcAc[a] R 0.33 | " | 2.1 | — | 48.3 | — | 51.7 | — | 98.3 |
| Rh(CO)$_2$AcAc[a] 0.33 | Bu$_4$POAc[c] 0.28 | 32 | 15.7 | 78.6 | — | — | 5.7 | |
| Rh(CO)$_2$AcAc[a] R 0.33 | Bu$_4$POAc[c] 0.28 | 31 | 16.9 | 62.1 | 20.9 | — | — | 98.6 |
| Rh(CO)$_2$AcAc[a] 0.33 | NaOAc 0.28 | 6 | 54.3 | — | 33.5 | 12.2 | — | |
| Rh(CO)$_2$AcAc[a] R 0.33 | NaOAc 0.28 | 11 | 36.5 | — | 32.6 | 30.9 | — | >67 |
| Rh(CO)$_2$AcAc[a] 0.33 | (Octyl)$_4$POAc 0.28 | 47 | 19.4 | 61.2 | 19.2 | — | — | |
| Rh(CO)$_2$AcAc[a] R 0.33 | (Octyl)$_4$POAc 0.28 | 65 | 17.4 | 42.6 | 30.6 | 0.5 | 9.0 | 99.1 |
| Rh(CO)$_2$AcAc[a] 0.33 | Bu$_4$PBr 0.28 | 31 | 16.1 | 63.0 | 9.6 | 1.0 | 10.2 | |
| Rh(CO)$_2$AcAc[a] R 0.33 | Bu$_4$PBr 0.28 | 35 | 22.6 | 47.4 | 29.5 | 0.4 | — | 97.6 |
| Rh(CO)$_2$AcAc[a] 0.33 | LiOAc 0.28 | 10 | 89.3 | — | 10.7 | — | — | |
| Rh(CO)$_2$AcAc[a] R 0.33 | LiOAc 0.28 | 4 | 28.3 | 5 | — | 66.7 | — | 96.8 |
| Rh(CO)$_2$AcAc[a] 0.33 | LiI 0.28 | 28 | 59.6 | 31.9 | 8.0 | — | — | |
| Rh(CO)$_2$AcAc[a] R 0.33 | LiI 0.28 | 14 | 71.0 | 24.1 | 2.5 | 2.3 | — | 98.8 |
| Rh(CO)$_2$AcAc[a] 0.33 | Bu$_4$POAc 0.56 | 60 | 12.5 | 66.6 | — | 7.1 | 13.8 | |
| Rh(CO)$_2$AcAc[a] R 0.33 | Bu$_4$POAc 0.56 | 66 | 8.4 | 27.2 | 64.4 | — | — | 99.2 |
| Rh(CO)$_2$AcAc[a] 0.33 | Bu$_4$NBr 0.28 | 20 | 48.3 | 9.5 | 22.2 | — | 20 | |
| Rh(CO)$_2$AcAc[a] R 0.33 | Bu$_4$NBr 0.28 | 35 | 46.9 | 10.7 | 36.1 | 2.1 | 4.2 | 98.8 |
| Rh$_4$(CO)$_{12}$ 0.083 | Bu$_4$POAc 0.28 | 35 | 46.6 | 21.5 | 29.4 | — | 2.4 | |
| Rh$_4$(CO)$_{12}$ R 0.083 | Bu$_4$POAc 0.28 | 66 | 26.0 | 3.4 | 70.6 | — | — | 98.9 |

[a]Dicarbonylacetylacetonato rhodium (I)
[b]AA = acetaldehyde
3-HPA = 3-hydroxypropionaldehyde
1,3-PDO = 1,3-propane diol
[c]Bu$_4$POAc = tetra-n-butylphosphonium acetate monoacetic acid
NaOAc = sodium acetate
(Octyl)$_4$POAc = tetraoctylphosphonium acetate
Bu$_4$PBr = tetrabutylphosphonium bromide
LiOAc = lithium acetate
[d]MTBE = methyl-t-butyl ether solvent.
[e]R in this column designates experiments using recycled rhodium catalyst present in the phase-separated methyl-t-butyl ether recovered from the experiment reported immediately above in the table.

We claim:
1. A process for preparing an alkanediol comprising the steps of:
   (a) contacting, at a temperature within the range of about 90 to about 125° C. and a pressure within the range of about 15 to about 5000 psig, an alkylene oxide with carbon monoxide and hydrogen in an essentially non-water miscible solvent in the presence of an effective amount of a non-phosphine-ligated rhodium catalyst and an effective amount of a catalyst promoter under reaction conditions effective to produce an intermediate product mixture comprising less than 15 wt % hydroxyaldehyde;
   (b) adding an aqueous liquid to said intermediate product mixture and extracting into said aqueous liquid a major portion of the hydroxyaldehyde at a temperature less than about 125° so as to provide an aqueous phase comprising the hydroxyaldehyde in greater concentration than the concentration of hydroxyaldehyde in the intermediate product mixture, and an organic phase comprising at least a portion of the rhodium catalyst or a rhodium-containing derivative thereof;
   (c) separating the aqueous phase from the organic phase;
   (d) contacting the aqueous phase comprising the hydroxyaldehyde with hydrogen in the presence of a hydrogenation catalyst at a pressure of at least about 100 psig and a temperature during at least a portion of the hydrogenation step of at least about 40° C. to provide a hydrogenation product mixture comprising an alkanediol; and

(e) recovering the alkanediol from the hydrogenation product mixture.

2. The process of claim 1 in which the solvent of step (a) comprises an ether.

3. The process of claim 1 in which the 3-hydroxypropanal in the intermediate product mixture is produced at a level within the range of about 5 to about 10 wt % based on said intermediate product mixture.

4. The process of claim 3 in which step (a) is carried out at a temperature within the range of about 100 to about 115° C.

5. The process of claim 4 in which step (a) is carried out at a pressure within the range of about 15 to about 1000 psig.

6. The process of claim 1 which further comprises carrying out steps (b) and (d) under carbon monoxide.

7. The process of claim 5 in which the solvent of step (a) has an Ostwald coefficient for carbon monoxide solubility greater than 0.15 v/v.

8. The process of claim 5 in which the solvent of step (a) comprises methyl-t-butyl ether.

9. The process of claim 1 in which the solvent of step (a) has a solubility in water at 25° C. of less than about 10%.

10. The process of claim 1 in which the promoter is water present in the reaction mixture in an amount within the range of about 1 to about 2.5 wt %.

11. The product of claim 1 in which the promoter is tetrabutylphosphonium acetate.

12. The process of claim 1 in which the alkylene oxide is ethylene oxide and the alkanediol is 1,3-propanediol.

13. The process of claim 11 in which the promoter is present in an amount within the range of about 0.01 to about 2.0 moles per mole of rhodium.

14. The process of claim 10 in which the carbon monoxide and hydrogen of step (a) are present in an $H_2/CO$ ratio within the range of about 1.5:1 to about 5:1.

15. The process of claim 10 in which the alkylene oxide is ethylene oxide and the alkanediol is 1,3-propanediol.

16. A process for preparing 1,3-propanediol comprising the steps of:

(a) reacting ethylene oxide, carbon monoxide and hydrogen in a solvent comprising methyl-t-butyl ether at a temperature within the range of about 90 to about 125° C. in the presence of a catalytic amount of a non-phosphine-ligated rhodium carbonyl and a promoting amount of at least one catalyst promoter, under hydroformylation conditions effective to produce an intermediate product mixture comprising less than 15 wt % 3-hydroxypropanal;

(b) adding, at a temperature within the range of about 25 to about 125° C., an aqueous liquid to said intermediate product mixture in an amount within the range of about 5 to about 20 weight percent based on the weight of the intermediate product mixture, and permitting the water-containing intermediate product mixture to resolve into an aqueous phase comprising 3-hydroxypropanal in a concentration of at least about 20 wt %, and an organic phase comprising a major portion of the rhodium;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature of at least about 40° C. to provide a hydrogenation product mixture comprising 1,3-propanediol; and (e) recovering 1,3-propanediol from the hydrogenation product mixture.

17. The process of claim 16 which further comprises removing any rhodium carbonyl from the aqueous phase of step (c).

18. The process of claim 16 in which the aqueous phase of step (b) comprises 3-hydroxypropanal in a concentration greater than about 35 wt %.

\* \* \* \* \*